(12) United States Patent
Lee et al.

(10) Patent No.: US 8,057,470 B2
(45) Date of Patent: Nov. 15, 2011

(54) INTEGRATED SMOKE EVACUATION ELECTROSURGICAL PENCIL AND METHOD

(75) Inventors: Alan R. Lee, Littleton, CO (US); Michael Biggs, Denver, CO (US)

(73) Assignee: ConMed Corporation, Utica, NY (US)

( * ) Notice: Subject to any disclaimer, the term of this patent is extended or adjusted under 35 U.S.C. 154(b) by 1111 days.

(21) Appl. No.: 11/897,457

(22) Filed: Aug. 30, 2007

(65) Prior Publication Data

US 2009/0062791 A1    Mar. 5, 2009

(51) Int. Cl.
*A61B 18/14* (2006.01)
(52) U.S. Cl. .............................. 606/41; 606/45
(58) Field of Classification Search ............ 606/41, 606/45, 49, 50
See application file for complete search history.

(56) References Cited

U.S. PATENT DOCUMENTS

| | | |
|---|---|---|
| 2,275,167 A | 3/1942 | Bierman |
| 2,828,747 A | 4/1958 | August |
| 3,906,955 A | 9/1975 | Roberts |
| 4,040,426 A | 8/1977 | Morrison, Jr. |
| 4,057,064 A | 11/1977 | Morrison, Jr. et al. |
| 4,060,088 A | 11/1977 | Morrison, Jr. et al. |
| 4,492,832 A | 1/1985 | Taylor |
| 4,562,838 A | 1/1986 | Walker |
| 4,719,914 A | 1/1988 | Johnson |
| 4,781,175 A | 11/1988 | McGreevy et al. |
| 4,834,095 A | 5/1989 | Miller |
| 4,911,159 A | 3/1990 | Johnson et al. |
| 5,066,294 A | 11/1991 | Cosmescu |
| 5,085,657 A | 2/1992 | Ben-Simhon |
| 5,088,997 A | 2/1992 | Delahuerga et al. |
| 5,098,430 A | 3/1992 | Fleenor |
| 5,108,389 A | 4/1992 | Cosmescu |
| 5,114,422 A | 5/1992 | Cosmescu |
| 5,154,709 A | 10/1992 | Johnson |
| 5,160,334 A | 11/1992 | Billings et al. |
| 5,186,714 A | 2/1993 | Boudreault et al. |
| 5,195,958 A | 3/1993 | Phillips |
| 5,197,963 A | 3/1993 | Parins |
| 5,199,944 A | 4/1993 | Cosmescu |
| 5,207,675 A | 5/1993 | Canady |
| 5,217,457 A | 6/1993 | Delahuerga et al. |
| 5,234,428 A | 8/1993 | Kaufman |
| 5,242,442 A | 9/1993 | Hirschfeld |

(Continued)

FOREIGN PATENT DOCUMENTS

AU    200071586 A1    5/2002

(Continued)

OTHER PUBLICATIONS

UK Search Report for Application No. GB0815571.5, dated Dec. 4, 2008, 2 pages.

(Continued)

*Primary Examiner* — Michael Peffley
*Assistant Examiner* — Samantha Good
(74) *Attorney, Agent, or Firm* — John R. Ley (57) ABSTRACT

An electrosurgical pencil includes an adjustable-length suction tube which surrounds a stationary electrode to evacuate smoke and electrosurgical byproducts from a surgical site. An electrode anchor unit is located within the interior of the suction tube to allow relative movement of the suction tube relative to a stationarily-retained electrode, and to receive and connect to different lengths of the electrodes. Adjusting the length of the suction tube relative to the different lengths of the electrode achieves effective evacuation, among other things.

16 Claims, 9 Drawing Sheets

U.S. PATENT DOCUMENTS

| | | | |
|---|---|---|---|
| 5,244,462 A | 9/1993 | Delahuerga et al. | |
| 5,273,524 A * | 12/1993 | Fox et al. | 604/21 |
| 5,306,238 A | 4/1994 | Fleenor | |
| 5,312,397 A | 5/1994 | Cosmescu | |
| 5,318,516 A | 6/1994 | Cosmescu | |
| 5,320,621 A | 6/1994 | Gordon et al. | |
| RE34,780 E | 11/1994 | Trenconsky et al. | |
| 5,413,575 A | 5/1995 | Haenggi | |
| 5,431,650 A | 7/1995 | Cosmescu | |
| 5,449,356 A | 9/1995 | Walbrink et al. | |
| 5,451,223 A | 9/1995 | Ben-Simhon | |
| 5,496,315 A | 3/1996 | Weaver et al. | |
| 5,505,710 A | 4/1996 | Dorsey, III | |
| 5,531,743 A | 7/1996 | Nettekoven et al. | |
| 5,674,219 A | 10/1997 | Monson et al. | |
| 5,693,044 A | 12/1997 | Cosmescu | |
| 5,720,745 A | 2/1998 | Farin et al. | |
| 5,792,139 A | 8/1998 | Chambers et al. | |
| 5,797,901 A | 8/1998 | Cosmescu | |
| 5,800,431 A | 9/1998 | Brown | |
| 5,836,909 A | 11/1998 | Cosmescu | |
| 5,836,944 A | 11/1998 | Cosmescu | |
| 5,951,548 A | 9/1999 | DeSisto et al. | |
| 6,039,736 A | 3/2000 | Platt, Jr. | |
| 6,063,081 A | 5/2000 | Mulier et al. | |
| 6,090,107 A | 7/2000 | Borgmeier et al. | |
| 6,099,525 A | 8/2000 | Cosmescu | |
| 6,142,995 A | 11/2000 | Cosmescu | |
| 6,149,648 A | 11/2000 | Cosmescu | |
| 6,197,026 B1 | 3/2001 | Farin et al. | |
| 6,258,088 B1 | 7/2001 | Tzonev et al. | |
| 6,293,945 B1 | 9/2001 | Parins et al. | |
| 6,302,881 B1 | 10/2001 | Farin | |
| 6,328,736 B1 | 12/2001 | Mulier et al. | |
| 6,355,034 B2 | 3/2002 | Cosmescu | |
| 6,391,027 B1 | 5/2002 | Farin et al. | |
| 6,458,125 B1 | 10/2002 | Cosmescu | |
| 6,475,216 B2 | 11/2002 | Mulier et al. | |
| 6,524,307 B1 | 2/2003 | Palmerton et al. | |
| 6,602,249 B1 | 8/2003 | Stoddard et al. | |
| 6,635,034 B1 | 10/2003 | Cosmescu | |
| 6,702,812 B2 | 3/2004 | Cosmescu | |
| 6,716,211 B2 | 4/2004 | Mulier et al. | |
| 6,852,112 B2 | 2/2005 | Platt | |
| 6,911,029 B2 | 6/2005 | Platt | |
| 7,004,939 B2 | 2/2006 | Mackay | |
| 7,033,353 B2 | 4/2006 | Stoddard et al. | |
| 7,083,601 B1 | 8/2006 | Cosmescu | |
| 7,112,199 B2 | 9/2006 | Cosmescu | |
| 7,198,625 B1 | 4/2007 | Hui et al. | |
| 2001/0051804 A1 | 12/2001 | Mulier et al. | |
| 2003/0181904 A1 | 9/2003 | Levine et al. | |
| 2004/0044342 A1 | 3/2004 | Mackay | |
| 2004/0162553 A1 | 8/2004 | Peng et al. | |
| 2004/0167512 A1 | 8/2004 | Stoddard et al. | |
| 2005/0113825 A1 | 5/2005 | Cosmescu | |

FOREIGN PATENT DOCUMENTS

| | | |
|---|---|---|
| CA | 2535467 A1 | 4/1993 |
| EP | 0545540 A1 | 6/1993 |
| EP | 1449487 A1 | 8/2004 |
| EP | 1602338 A2 | 12/2005 |
| GB | 671497 | 5/1952 |
| GB | 1014995 | 12/1965 |
| GB | 1165148 | 9/1969 |
| WO | WO92/22258 A1 | 12/1992 |
| WO | WO98/14131 A1 | 4/1998 |
| WO | WO03/061499 A1 | 7/2003 |
| WO | WO2007/129321 A2 | 11/2007 |

OTHER PUBLICATIONS

Siemens, Electromedicine Compendium, publication, 1978, 6 pgs., Heinz Kresse—Publisher, Germany.

* cited by examiner

INTEGRATED SMOKE EVACUATION ELECTROSURGICAL PENCIL AND METHOD

This invention relates to electrosurgery, and more specifically, to a new and improved electrosurgical pencil with integrated smoke evacuation capability which permits the use of different length electrodes and the adjustment in position of a surrounding smoke evacuation tube in relation to the electrode.

BACKGROUND OF THE INVENTION

An electrosurgical pencil is a medical instrument which uses an electrode to apply a high-voltage, high-frequency electrical current to tissue to achieve a surgical effect, such as cutting of tissue and/or coagulation of blood oozing from the cut or lacerated tissue. During an electrosurgical procedure, applying the high-voltage, high-frequency electrical current to the tissue produces electrosurgical byproducts, which consist principally of smoke and which also include other debris. Because the smoke and debris may contain small amounts of pathogenic particles, inhalation by the surgical staff is undesirable and may present health concerns for the surgical staff. The smoke may also obstruct the surgeon's view of the surgical site and thus may impede progress in completing the electrosurgical procedure.

Smoke evacuators have been developed to remove the undesirable smoke and electrosurgical byproducts from the surgical site. A smoke evacuator includes a fan which develops a source of low pressure air which is conducted through a suction hose to the surgical site. The airflow created by the low-pressure source evacuates smoke and electrosurgical byproducts from the surgical site into an open end of the suction hose. The electrosurgical byproducts carried by the airflow are passed through a filter, which removes smoke, particulate debris and other electrosurgical byproducts, including odors, before the filtered air is discharged at a location remote from the surgical site but still within the surgical operating room.

While smoke evacuators are generally effective in removing the smoke and electrosurgical byproducts, using a smoke evacuator is accompanied by certain disadvantages. The open end of the suction hose must be maintained at the surgical site where the electrode delivers the high-voltage, high-frequency current to the tissue. A surgical staff person other than the surgeon must usually hold and manipulate the end of the suction hose while the surgeon manipulates the electrosurgical pencil during the medical procedure. In many types of medical procedures, the surgical site is not openly accessible and therefore it is impossible or difficult to place the open end of the suction hose adjacent to the surgical site while the surgeon is manipulating the electrode at the surgical site. Under such circumstances, some smoke or debris may escape evacuation. Placing the end of the suction hose at the surgical site may also obscure or limit the surgeon's view of the surgical site or make it difficult to manipulate the electrode in tight spaces caused by the presence of the end of the suction hose. Lastly, among other things, the suction hose, which extends within the operating room, and the smoke evacuator are additional pieces of equipment which must be dealt with in an already-congested operating room, thereby complicating the surgical procedure.

To avoid many of the physical complications and obstructions associated with a separate suction hose, a suction tube has been attached to the electrosurgical pencil with an open end of the suction tube located adjacent to the electrode. The suction hose from the fan low-pressure air source is connected to the electrosurgical pencil and to the suction tube. In this manner, the open end of the suction tube is always located adjacent to the electrode at the surgical site where the smoke and other electrosurgical byproducts are created. The suction tube is always maneuvered close to the surgical site as a consequence of manipulating the electrosurgical pencil during the procedure. A separate surgical staff person is not required to position the end of the suction hose, because the surgeon inherently maneuvers the end of the suction tube while manipulating the electrosurgical pencil. The suction tube evacuates the electrosurgical byproducts from the surgical site as those byproducts are produced.

Suction tubes have been combined with electrosurgical pencils in at least two different ways. One way involves creating an external clip-on shroud-like structure which connects to a standard electrosurgical pencil. A shroud is located adjacent to the electrode and contains its own flow passageway for evacuating the smoke and other electrosurgical byproducts. The shroud is connected by the suction hose to the low-pressure air source. Connecting the shroud to the electrosurgical pencil changes the size of the pencil and may make the electrosurgical pencil itself more awkward to hold and manipulate by the surgeon. The other way of combining a suction tube with an electrosurgical pencil is to integrate the suction tube as part of the structure of the electrosurgical pencil. In this circumstance, the suction tube is built into a handle or housing of the electrosurgical pencil. The integration of the suction tube with the pencil has the effect of eliminating the more bulky and somewhat awkward aspects of connecting a separate shroud to the electrosurgical pencil, and also eliminates the risk or possibility that the separate shroud will become disconnected from the pencil. However, manufacturing of the electrosurgical pencil is complicated as a result of integrating the suction tube and creating a flow passageway within the housing of the electrosurgical pencil for the evacuated smoke, debris and other electrosurgical byproducts.

One of the consequences of integrating the suction tube with the electrosurgical pencil is that the size of the suction tube may become relatively small. The size of a typical electrosurgical pencil simply will not accommodate a relatively large suction tube. Consequently, to be most effective in evacuating the electrosurgical byproducts, the open end of the suction tube must be positioned as close as possible to the surgical site and the electrode. A closely-located suction tube captures the airborne byproducts almost immediately after formation at the surgical site and before the byproducts can diffuse from the surgical site to an extent that effective evacuation becomes impossible.

One way of integrating the suction tube with the electrosurgical pencil is to position the entire suction tube laterally adjacent to the tip of the electrode. While this configuration is effective in some circumstances, the evacuation area adjacent to the end of the suction tube is laterally displaced from the tip of the electrode, thereby providing a greater opportunity for the electrosurgical byproducts to escape evacuation on the opposite lateral side of the electrode. In addition, having the suction tube extending laterally adjacent to the tip of the electrode may limit the ability of the surgeon to manipulate the electrode in close and confined surgical sites.

Electrosurgical pencils with a laterally positioned suction tube have also been constructed to permit selective extension or retraction of the suction tube. Selective extension or retraction of the suction tube allows the surgeon to position the open end of the suction tube close to the surgical site for more effective evacuation, or allows the end of the suction tube to be retracted from the tip of the electrode if the surgical site is confined or if the suction tube obscures the surgeon's vision of the surgical site. When the end of the suction tube is positioned further away from the tip of the electrode, the evacuation of the airborne electrosurgical byproducts is less effective and the electrosurgical byproducts are more likely to diffuse into the surrounding operating room environment without being captured.

A selectively extendable and retractable suction tube also more readily accommodates the use of different-length electrodes with the electrosurgical pencil. Depending upon the medical procedure or the state of the procedure, the surgeon may require the use of a longer electrode to extend the electrode to a surgical site. A variety of different length electrodes may be used during a single medical procedure, and in such circumstances, the ability to adjust the length and position of the suction tube relative to the tip of the electrode assures more effective evacuation of the electrosurgical byproducts than in those circumstances where the position of the suction tube cannot be adjusted relative to the tip of the electrode.

One way of integrating a somewhat larger suction tube in an electrosurgical pencil is to locate the electrode within the open end of the suction tube. Under such circumstances, the suction tube and the electrode occupy the same space within the electrosurgical pencil. Locating the electrode within the suction tube is relatively easily accomplished if the suction tube is fixed and not selectively extendable and retractable, because the socket or receptacle which receives and connects the electrode is in a fixed position relative to the suction tube. The fixed relative position eliminates the benefits of selective extension and retraction of the suction tube to achieve the most effective evacuation relative to different lengths of the electrode.

Instead of being fixed to the electrosurgical pencil housing, the suction tube may be made selectively extendable and retractable while maintaining the electrode within the open end of the suction tube. In this circumstance the electrode connection socket or receptacle is also fixed at or near the open end of the suction tube. The suction tube can be extended when it is desired to extend the tip of the electrode from the housing of the electrosurgical pencil itself. However, the open end of the suction tube is maintained in fixed relationship to the tip of the electrode, because the electrode moves in conjunction with the suction tube. The open end of the suction tube cannot be adjusted relative to the tip of the electrode to achieve the most effective evacuation. In a particularly confined surgical site, the extension of the suction tube may not be permitted because of space limitations. In such circumstances, a relatively long electrode may be used. Although the longer electrode can be substituted for a shorter electrode, the suction tube cannot be extended relative to the tip of the longer electrode because of the socket or receptacle for the electrode occupies a fixed position relative to the suction tube. The use of a longer electrode greatly diminishes the smoke evacuation efficiency because the tip of the electrode is spaced a greater distance from the open end of the suction tube.

It has been recognized that it would be desirable to locate the electrode within the interior of an extendable and retractable suction tube, to permit selective extension and retraction of the suction tube relative to electrodes of different length. However, retaining the electrode within the center of the suction tube while still permitting the suction tube to extend and retract relative to the stationary electrode is a complex matter.

SUMMARY OF THE INVENTION

The present invention effectively locates an electrode within the open end of a selectively extendable and retractable suction tube in a such a way that the open end of the suction tube can be adjusted relative to electrosurgical electrodes of different lengths. Adjusting the suction tube relative to different electrodes achieves the most effective evacuation of smoke, debris and other electrosurgical byproduct from the electrosurgical site, for all of the different-length electrodes. Electrodes of different lengths may still be used in accordance with the requirements of the surgical procedure, without compromising the evacuation capability or the surgical procedure.

In accordance with these and other features, one aspect of the invention involves an electrosurgical pencil for delivering electrical energy from an electrode to tissue at an electrosurgical site and for evacuating electrosurgical byproducts from the site created by delivering the electrical energy to the tissue. The electrosurgical pencil includes a pencil housing and a suction tube which is movably positioned by the housing. The suction tube defines an interior passageway which surrounds the electrode and through which the byproducts are evacuated. A distal end of the suction tube extends and retracts outside of the housing and relative to the electrode while a proximal end of the suction tube remains within the housing. An electrode anchor unit is located stationarily relative to the housing within the interior passageway of the suction tube. The electrode anchor unit includes having a socket member by which to connect and disconnect the electrode. The stationary location of the electrode anchor unit permits the relative extension and retraction of the suction tube. An airflow connector on the housing communicates low-pressure air to the interior passageway of the suction tube for evacuating the byproducts from the surgical site, and an electrical connector is connected to the socket member to deliver the electrical energy to the electrode.

Another aspect of the invention involves a method of supporting an electrode in an electrosurgical pencil to deliver electrosurgical energy to tissue at an electrosurgical site while evacuating electrosurgical byproducts from the site created by delivering the electrical energy to the tissue. The method comprises movably positioning a suction tube within the pencil to surround the electrode and define an interior passageway around the electrode by which to evacuate the byproducts from the surgical site, positioning an electrode anchor unit within the interior passageway of the suction tube to permit movement of the suction tube relative to the anchor unit, stationarily anchoring the electrode anchor unit to the electrosurgical pencil to permit movement of the suction tube relative to the anchor unit, connecting the electrode to the anchor unit, and extending and retracting the suction tube relative to the electrode connected to the anchor unit to establish a selected degree of exposure of the electrode beyond an end of the suction tube.

Further subsidiary features of the invention involve connecting electrodes having different lengths to the anchor unit and extending and retracting the suction tube with respect to each of the different-length electrodes; using a collet member, a socket member and an anchor rod as part of the anchor unit, supporting the collet member within the interior passageway by movable contact with the suction tube, supporting the socket member within the collet member, and extending the anchor rod from the socket member and the collet member to the pencil to stationarily anchor the anchor unit without interfering with the movement of the suction tube; substantially inhibiting rotational and longitudinal movement of the collet member and the socket member relative to the interior passageway; using bent ends of the anchor rod to inhibit rotational torsion of the collet member and the socket member relative to the pencil; and conducting the electrosurgical energy through the anchor rod to the electrode; among other things.

A more complete appreciation of the present invention and its scope, and the manner in which it achieves the above and other features and improvements, can be obtained from the following detailed description of a presently preferred embodiment taken in connection with the accompanying drawings, which are briefly summarized below, and from the appended claims.

DETAILED DESCRIPTION

Figure 1:
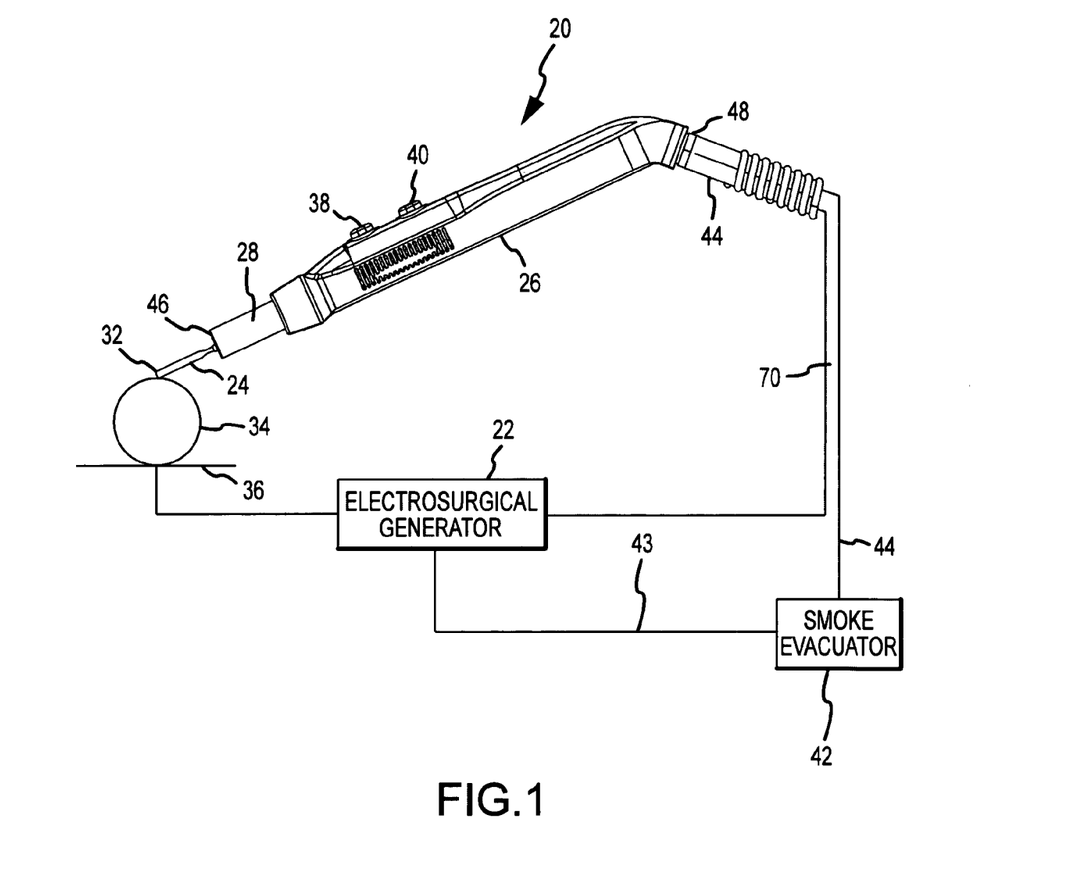
FIG. 1 is a side elevational view of a smoke evacuation electrosurgical pencil with an integrated suction tube which incorporates the present invention, shown connected to an electrosurgical generator and a smoke evacuator illustrated in block diagram form.

An electrosurgical pencil 20 which embodies the present invention is generally shown in FIG. 1. The electrosurgical pencil 20 receives electrical power from a conventional electrosurgical generator 22 or power source. An electrode 24 extends from a housing 26 of the electrosurgical pencil 20. A slidable suction tube 28 surrounds the electrode 24 and also extends from the housing 26. To use the pencil 20 in an electrosurgical procedure, a tip 32 of the electrode 24 is applied to tissue 34 of a patient at a surgical site to deliver high-voltage, high- or radio-frequency (RF) current from the electrosurgical generator 22 to the tissue 34. The RF current is conducted through the tissue 34 to a return electrode 36, which contacts the tissue 34, and from the return pad or return electrode 36 back to the generator 22, thereby completing an electrical circuit. The characteristics of the waveforms of RF current create an electrosurgical cutting or coagulation effect on the tissue. The characteristics of the waveform of RF current are selected at the electrosurgical generator 22, and the delivery of the RF waveform is controlled by depressing cut and coagulation switch buttons 38 and 40 on the housing 26 of the pencil 20.

Depressing one of the buttons 38 or 40 activates the electrosurgical generator 22 to deliver the RF waveform and also activates a conventional smoke evacuator 42 by a signal conducted over a conductor 43. The typical smoke evacuator 42 includes a fan (not shown) which creates a low pressure air source that creates an evacuation airflow from the surgical site. A suction hose 44 conducts the evacuation airflow from the suction tube 28 through the interior of the housing 26 and into an interior passageway 45 (FIGS. 6 and 7) of the suction tube 28, and then to the smoke evacuator 42. The low pressure air from the smoke evacuator 42 is communicated within the interior of the housing 26 and into the interior of the suction tube 28. The low pressure airflow develops sufficient suction at a distal end 46 of the suction tube 28 to remove the smoke, debris and electrosurgical byproducts from the surgical site generated when the RF current waveform is applied to the tissue 34. The flow of low pressure air is also sufficient to convey the smoke, debris and electrosurgical byproducts from the surgical site through the passageway 45 (FIGS. 6 and 7) and the housing 26 through the suction hose 44 to the smoke evacuator 42. A filter and deodorizing module (neither shown) are located in the smoke evacuator 42 to remove the electrosurgical byproducts and odors from the air, before that cleaned and deodorized air is discharged from the smoke evacuator 42.

Figure 2:
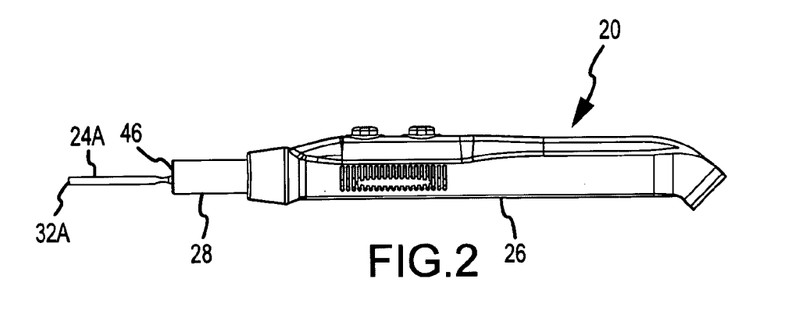
FIG. 2 is a side elevational view of the electrosurgical pencil shown in FIG. 1 with a relatively short electrode and a slidable suction tube of the electrosurgical pencil shown in a retracted position.
Figure 3:
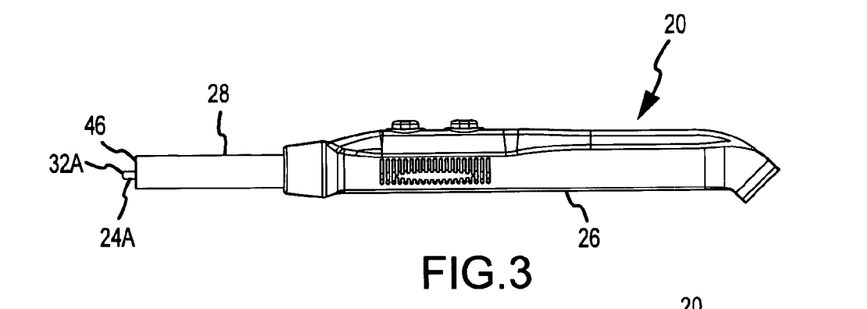
FIG. 3 is a side elevational view of the electrosurgical pencil shown in FIG. 2 with the slidable suction tube shown in an extended position which covers all but a tip end portion of the relatively short electrode.
Figure 4:
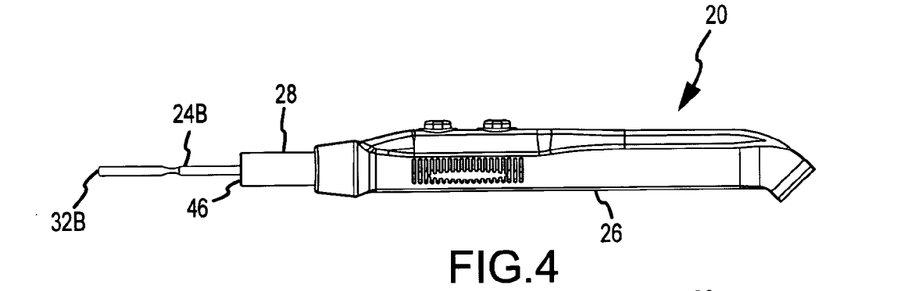
FIG. 4 is a side elevational view of the electrosurgical pencil shown in FIG. 1 with a relatively long electrode and the slidable suction tube shown in a retracted position.
Figure 5:
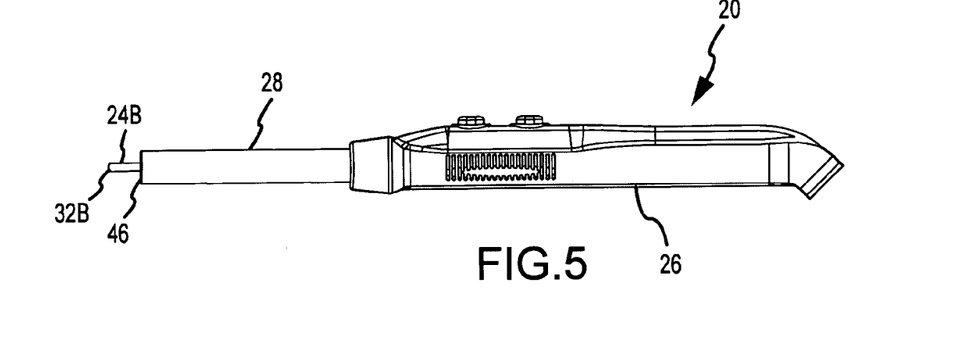
FIG. 5 is a side elevational view of the electrosurgical pencil shown in FIG. 4 with the slidable suction tube shown in an extended position which covers all but a tip end of the relatively long electrode.

The extent and effectiveness in evacuating the electrosurgical byproducts is maximized or otherwise controlled by manually extending or retracting the suction tube 28 relative to the housing 26, thereby moving the distal end 46 of the suction tube 28 relative to the electrode tip 32. This effectiveness and versatility is illustrated in FIGS. 2-5. Electrodes of different lengths can be attached to and detached from the electrosurgical pencil 20, as illustrated by a relatively short electrosurgical electrode 24A which has an electrode tip 32A (FIGS. 2 and 3) and by a relatively long electrosurgical electrode 24B which has an electrode tip 32B (FIGS. 4 and 5). The suction tube 28 surrounds the length of either electrode 24A or 24B connected to the pencil 20, and is longitudinally extendable and retractable relative to any length of electrode. FIGS. 2 and 4 show a relatively retracted position of the suction tube 28 relative to the housing 26. In the retracted position, the effectiveness of the suction tube 28 in evacuating smoke and electrosurgical byproducts from the electrosurgical site may be limited depending upon the length of the electrode. For example, with respect to the relatively long electrode 24B, the tip 32B is displaced a substantial distance from the distal end 46 of the retracted suction tube 28 (FIG. 4), thereby diminishing the evacuation capability because of the significant distance between the distal end 46 of the suction tube 28 and the electrode tip 32B. The effectiveness of the evacuation of smoke is increased when the distal end 46 of the suction tube 28 is extended to a position near or adjacent to the electrode tips 32A and 32B (FIGS. 3 and 5).

Figure 6:
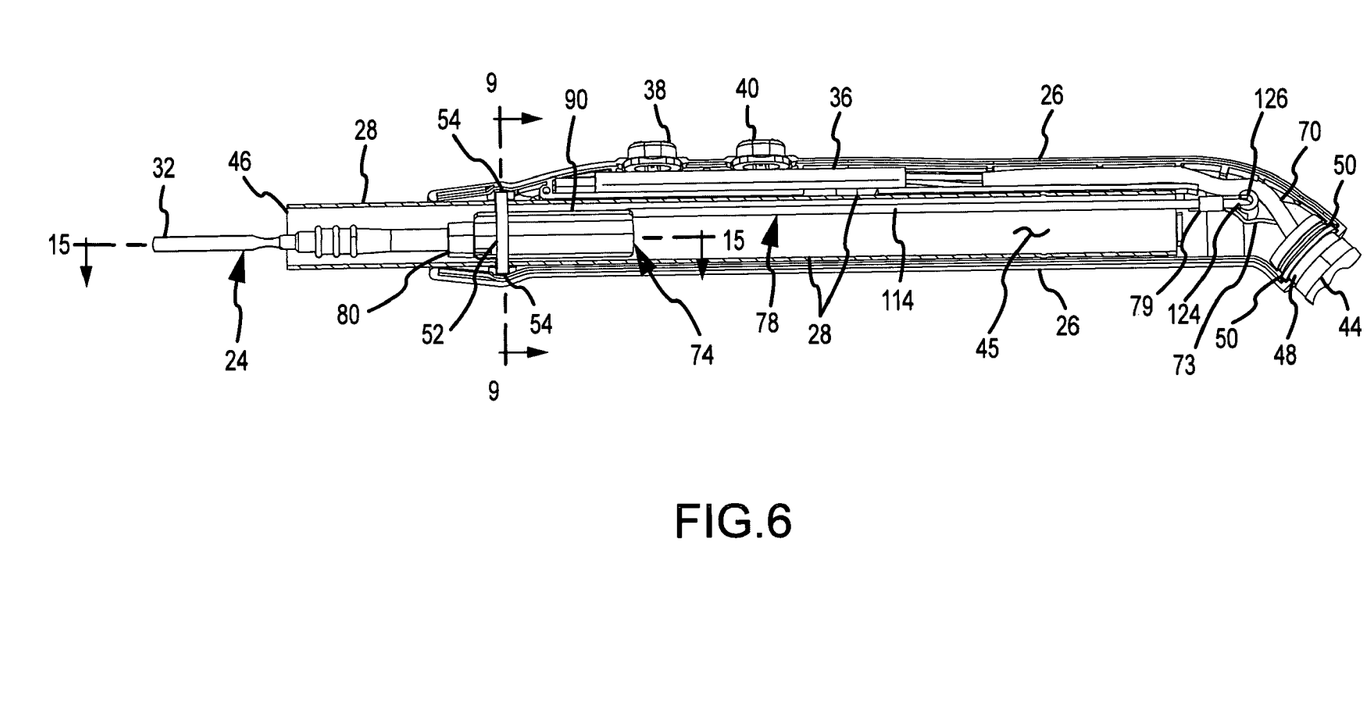
FIG. 6 is an enlarged vertical and longitudinal cross-sectional view of the electrosurgical pencil shown in FIGS. 1 and 2, with the electrode and an electrode anchor unit shown in elevation.
Figure 7:
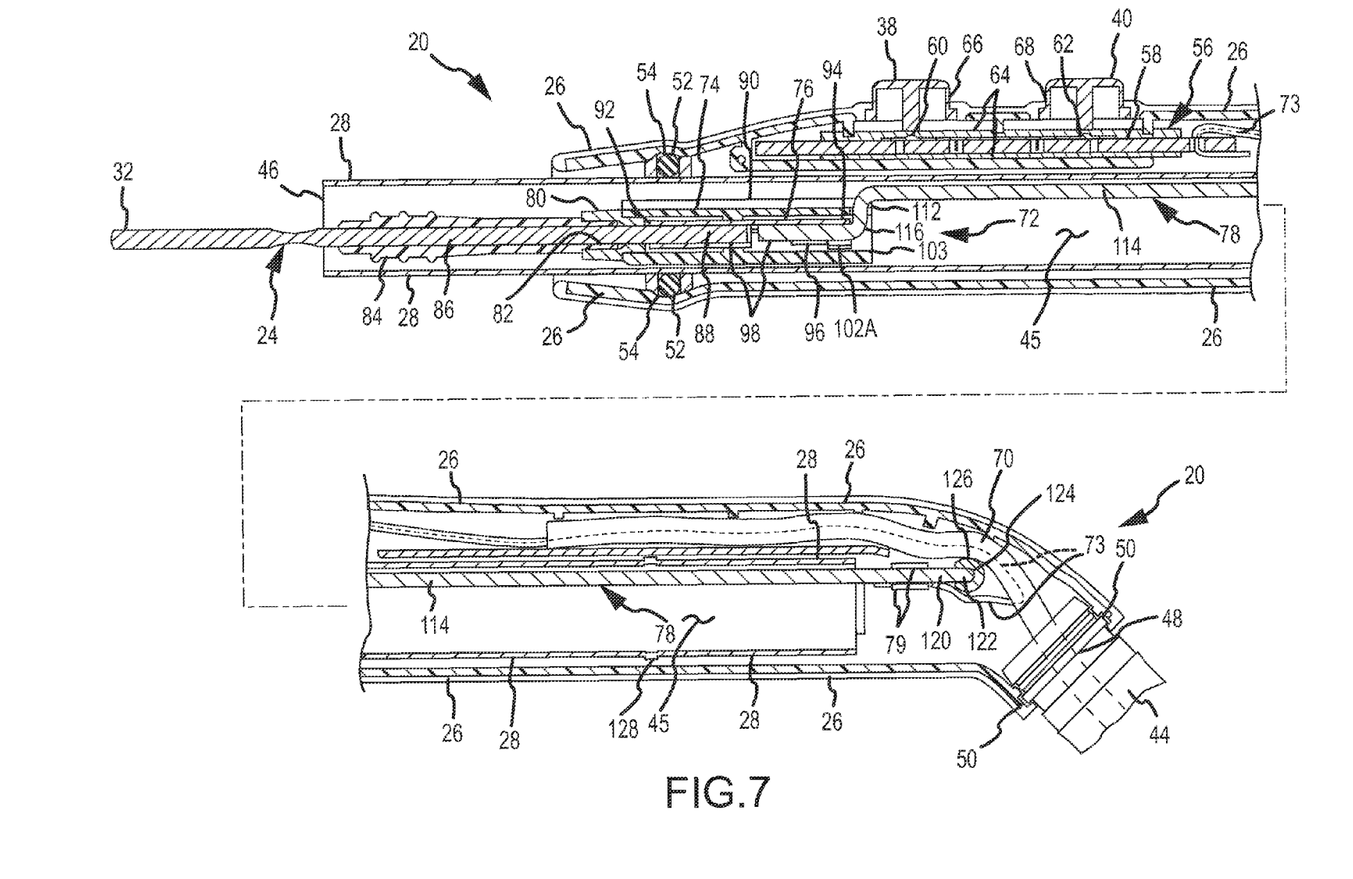
FIG. 7 is an enlarged, broken-apart and complete cross-sectional view of the electrosurgical pencil shown in FIG. 6.
Figure 8:
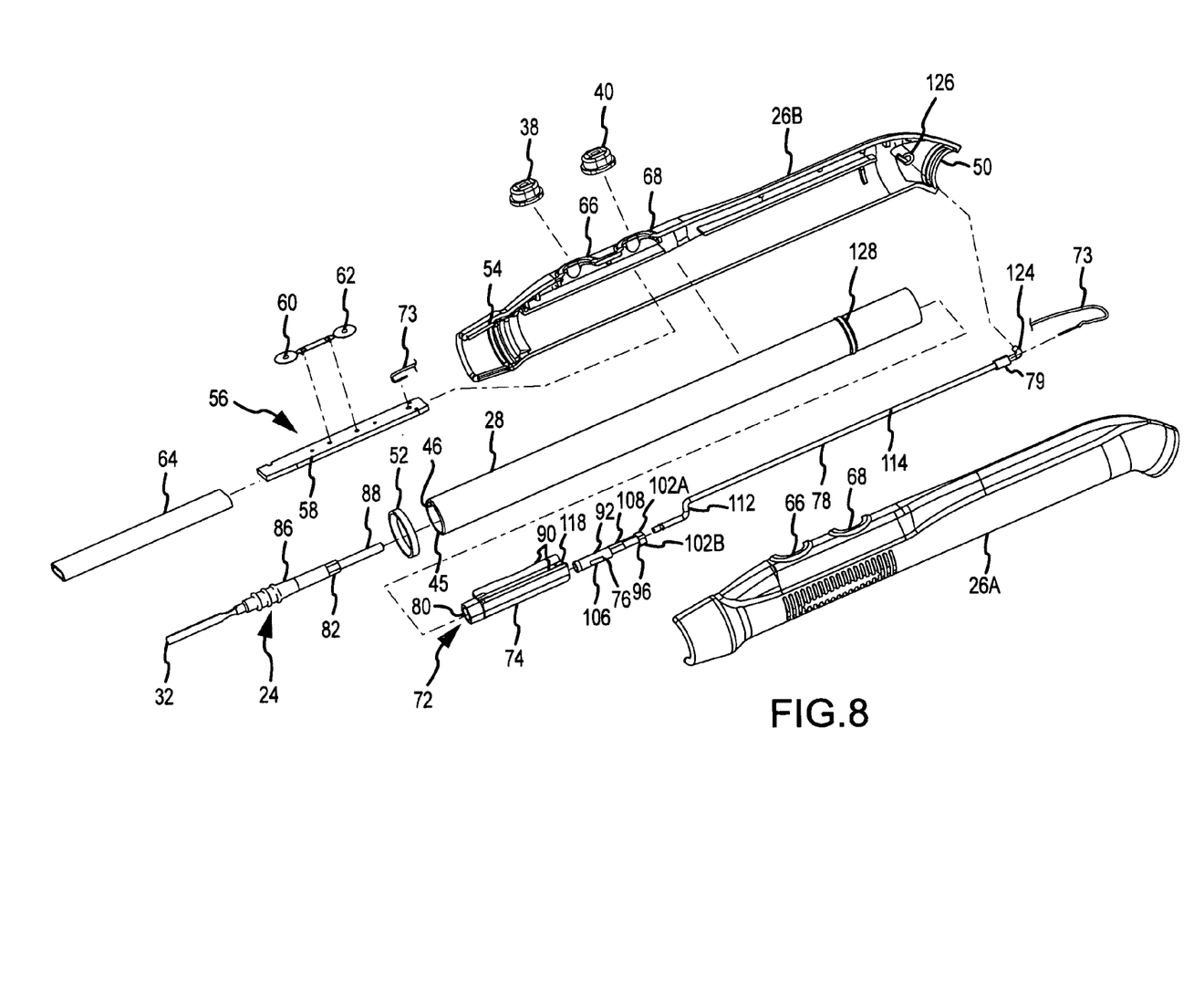
FIG. 8 is an exploded view of the electrosurgical pencil shown in FIGS. 1 and 2.

The interior of the housing 26 of the pencil 20 includes sufficient space or volume to receive the suction tube 28, and to allow the suction tube 28 to extend and retract within the housing 26, as shown in FIGS. 6-8. A swivel 48 (FIGS. 6 and 7) connects the suction hose 44 to the rear or proximal end of the housing 26. The swivel 48 allows the suction hose 44 to rotate relative to the housing 26 as the surgeon manipulates the pencil 20, thereby diminishing the amount of resistance to free movement of the pencil 20 caused by the connection and twisting of the suction hose 44. The swivel 48 is held in position in the housing 26 as a result of a flange of the swivel 48 extending into grooves 50 formed at the proximal end of halves 26A and 26B of the housing 26 (FIGS. 1 and 8). The housing halves 26A and 26B are ultrasonically welded together to complete the housing 26 and to hold the interior components of the pencil 20 within the housing 26.

The suction tube 28 is sealed to the interior of the housing 26 by an O-ring 52. The O-ring 52 contacts and encircles the exterior of the suction tube 28 at a front or distal end of the housing 26. The O-ring 52 fits within grooves 54 formed in the housing halves 26A and 26B. Positioned in this manner, the low pressure air communicated through the suction hose 44 to the interior of the housing 26 does not escape around the opening in the distal end of the housing 26 from which the suction tube 28 extends. The O-ring 52 causes low pressure air within the housing interior to be communicated through the interior passageway 45 of the suction tube 28 to the distal end 46 of the suction tube.

A switch module 56 is also located within the interior of the housing 26 and is supported between the housing halves 26A and 26B. The switch module 56 is of conventional construction and supports the buttons 38 and 40. The switch module 56 includes a printed circuit board 58 upon which two dome switches 60 and 62 are positioned by tangs (not shown) above circuit traces (not shown) on the printed circuit board 58. A resilient sleeve 64, preferably made of silicone, encloses the printed circuit board 58 and the dome switches 60 and 62, thereby holding the dome switches 60 and 62 in position relative to the circuit traces. When the switch module 56 is retained within the interior of the housing 26, the buttons 38 and 40 are located above over the dome switches 60 and 62, respectively, as a result of the buttons 38 and 40 fitting within openings 66 and 68 formed in the housing halves 26A and 26B. The resilient sleeve 64 acts as a gasket to prevent the escape of low pressure air from the interior of the housing 26 at the buttons 38 and 40 and to prevent the smoke and other debris from contaminating the switches 60 and 62.

When the button 38 is depressed, force is transmitted through the sleeve 64 to the dome switch 60, causing the dome switch 60 to deflect and create an electrical contact between circuit traces on the printed circuit board 58. Similarly, depressing the button 40 causes the dome switch 62 to create an electrical circuit. Electrical signals created by depressing buttons 38 and 40 are conducted to the electrosurgical generator 22 over conductors 70 (FIG. 1) which extend through the swivel 48 and exit from the suction hose 44 through a conventional exit fitting (not shown) to connect to the electrosurgical generator 22 (FIG. 1). Three separate electrical conductors are represented at 70 (FIG. 1). One electrical conductor conducts a signal created by depressing one button 38, and another electrical conductor conducts a signal created by depressing the other button 40. The signals created by depressing the buttons 38 and 40 represent the selection of a cutting RF waveform or a coagulation RF waveform. A third electrical conductor represented at 70 (FIG. 1) delivers the selected RF waveform from the electrosurgical generator 22 to the pencil 20 and the printed circuit board 58. Extending the conductors 70 through the swivel 48 and the suction hose 44 to the exit fitting (not shown) reduces the number of unconfined elements which must be dealt with at the surgical site when the electrosurgical pencil 20 is used.

Figure 9:
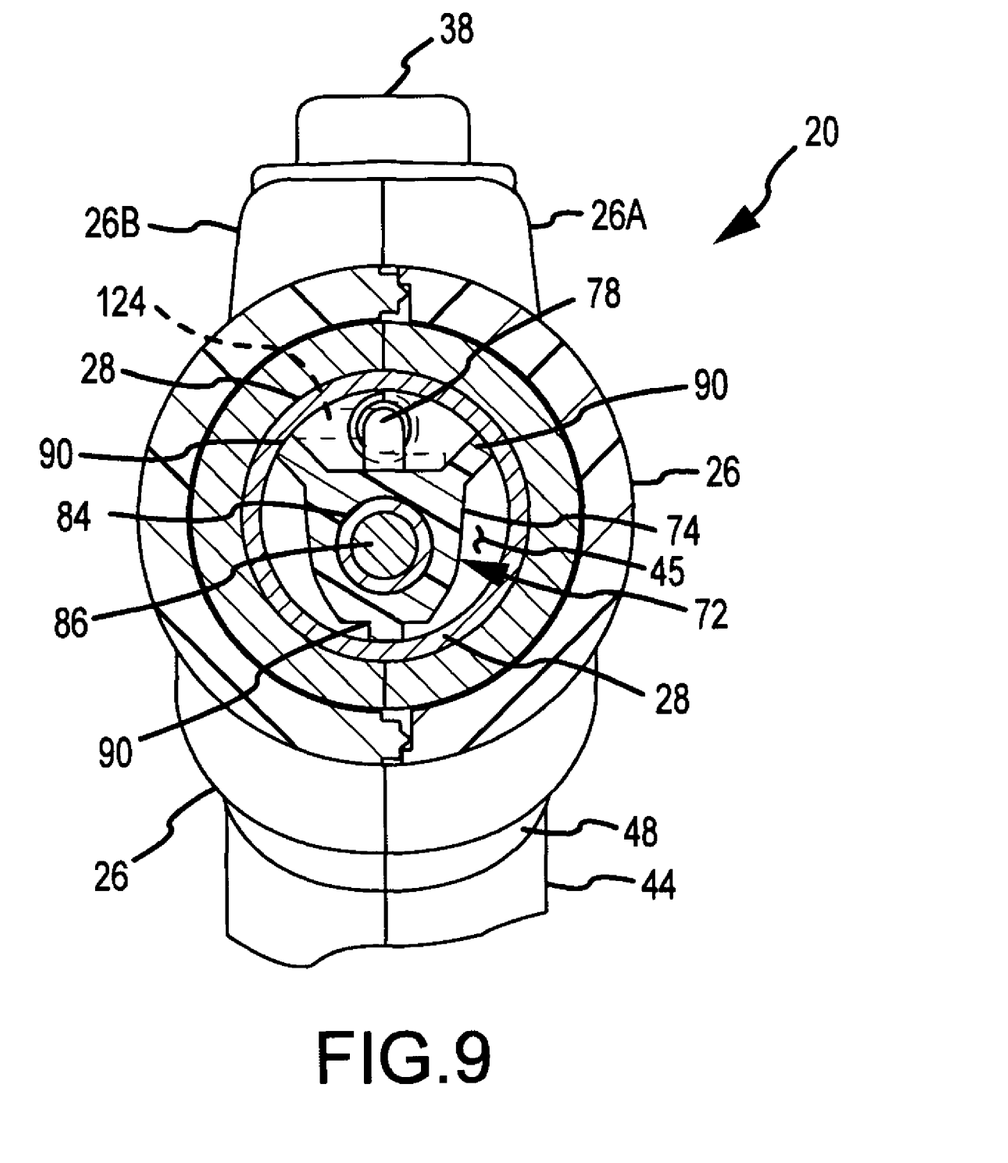
FIG. 9 is an enlarged cross-sectional view of the electrosurgical pencil taken substantially in the plane of line 9-9 in FIG. 6.

The RF electrosurgical waveform delivered from the electrosurgical generator 22 is conducted to the electrode 24 through an electrode anchor unit 72 of the pencil 20. The electrode anchor unit 72 is located substantially within the suction tube 28, as shown in FIG. 9. The electrode anchor unit 72 retains and supports the electrode 24 in a stationary position relative to the housing 26 of the pencil 20. A wire 73 conducts the RF electrosurgical waveform from the printed circuit board 58 to the electrode anchor unit 72. More details concerning the electrode anchor unit 72 are shown and discussed in conjunction with FIGS. 9-15.

The electrode anchor unit 72 comprises an electrically insulating collet member 74, an electrically conductive socket member 76, and an electrically conductive anchor rod 78. A collet member 74 receives and supports the electrode 24. The socket member 76 is located within the collet member 74 and electrically connects to the electrode 24. The anchor rod 78 mechanically connects the collet member 74 and the housing 26 in a manner which permits the suction tube 28 to be extended and retracted relative to the stationary electrode anchor unit 72. The electrode anchor unit 72 mechanically supports the collet member 74 and the electrode 24 to resist longitudinal and rotational movement relative to the housing 26 while permitting extension and retraction of the suction tube 28. The anchor rod 78 is also electrically connected to conduct the RF electrosurgical waveform delivered from the electrosurgical generator 22 and the conductor 73 to the socket member 76. The conductor 73 is connected to the rod 78 by a crimped connector sleeve 79. RF electrosurgical waveform is conducted from the socket member 76 to the electrode 24 where it is applied to the tissue 34 (FIG. 1).

The forward or distal end of the collet member 74 includes a hexagonal-shaped receptacle 80 which receives a correspondingly-shaped hexagonal surface 82 formed on a rear or proximal end of an insulator 84 which covers a portion of a metal body 86 of the electrode 24, as shown in FIGS. 7-11 and 15. The engagement of the hexagonal-shaped receptacle 80 and surface 82 prevents the electrode 24 from rotating relative to the collet member 74 and also maintains the electrode 24 connected to the collet member 74. A rear or proximal end 88 of a metal body 86 of the electrode 34 also contacts and fits within the socket member 76 when the hexagonal-shaped receptacle 80 and surface 82 are engaged. The frictional contact of the rear end 88 of the metal body 86 with the socket member 76 further assists in maintaining the electrode 24 in the retained position within the collet member 74, but does permit separation of the electrode 24 when desired.

The collet member 74 includes ribs 90 which extend radially outward from the collet member 74 at circumferentially displaced locations, as shown in FIGS. 9-12. The outer edges of the ribs 90 contact an interior surface (FIG. 9) of the suction tube 28, and thereby stabilize and locate the collet member 74 relative to the suction tube 28. The degree of frictional contact of the outer edges of the ribs 90 with the interior surface of the suction tube 28 does not inhibit the sliding of the suction tube 28 relative to the collet member 74. The collet member 74 remains stationary with respect to the pencil housing 26 as the suction tube 28 slides relative to it because the anchor rod 78 holds the collet member 74 stationary relative to the pencil housing 26.

Figures 10, 11:
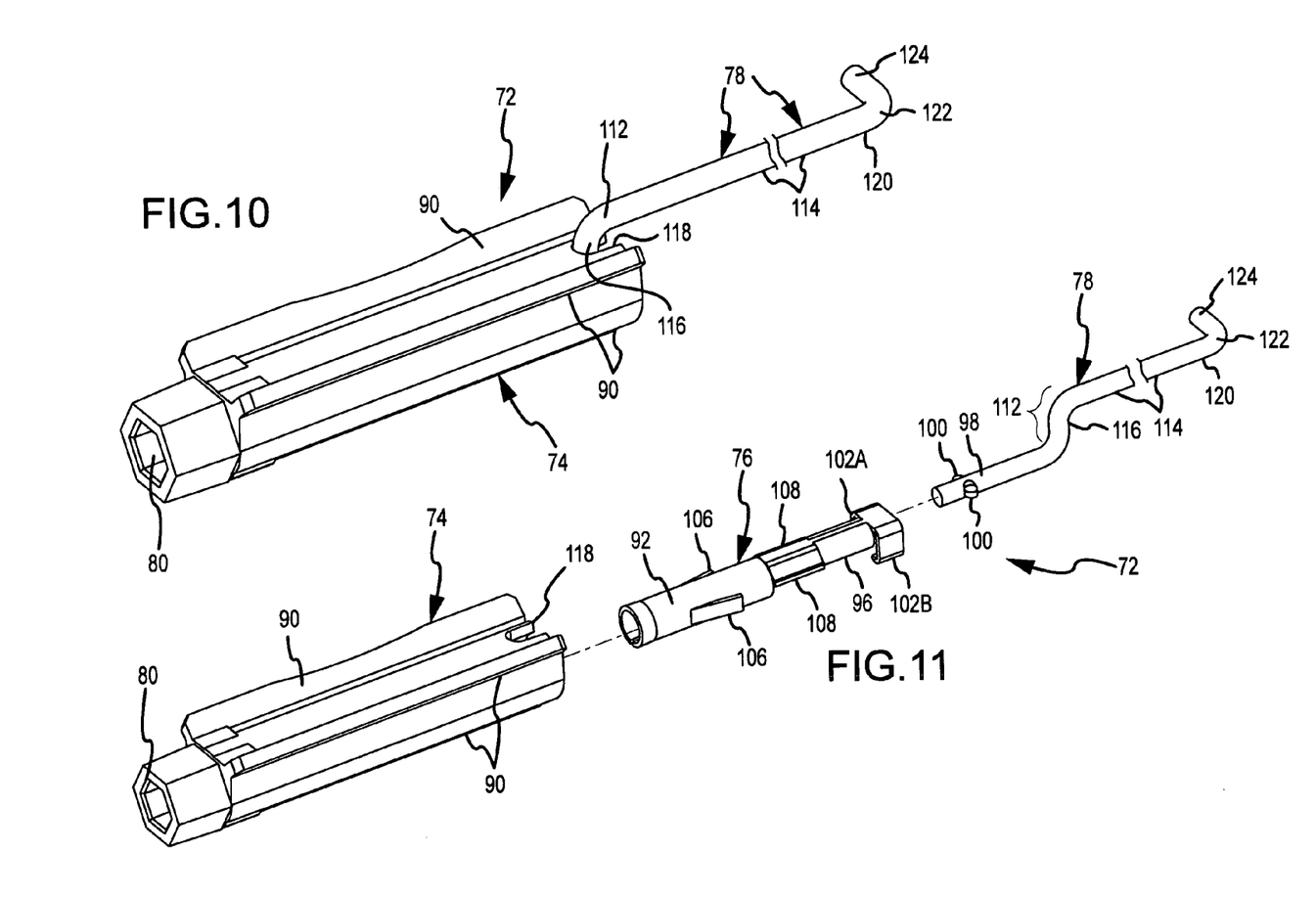
FIG. 10 is an enlarged perspective view of an electrode anchor unit of the electrosurgical pencil shown in FIGS. 6-9.
FIG. 11 is an exploded view of the electrode anchor unit shown in FIG. 10.
Figure 13:
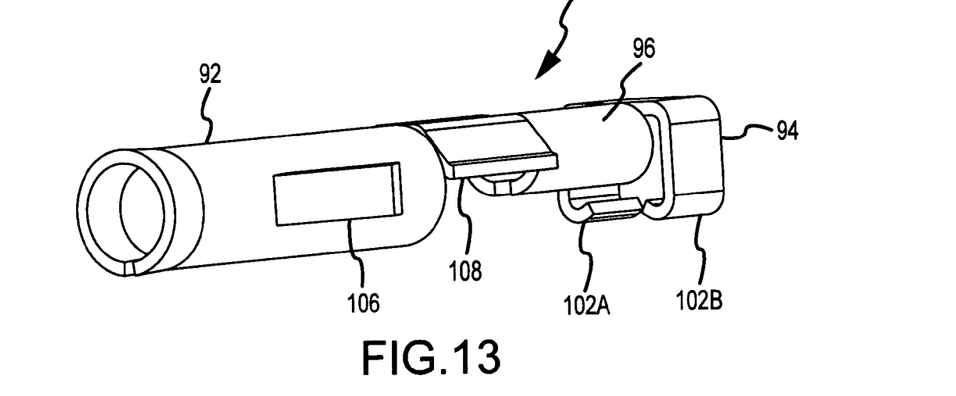
FIG. 13 is a perspective view of a socket member of the electrode anchor unit shown in FIGS. 10 and 11.
Figure 14:
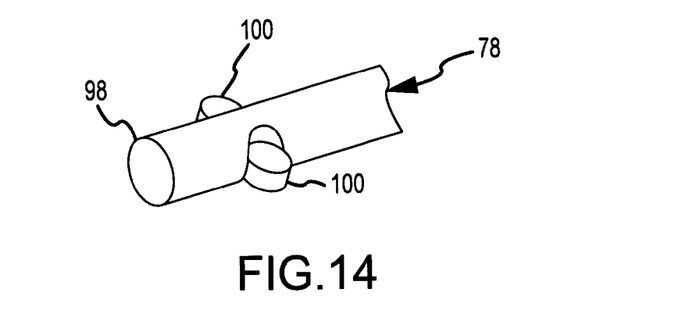
FIG. 14 is a perspective view of a front end of an anchor rod of the electrode anchor unit shown in FIGS. 10 and 11.
Figure 15:
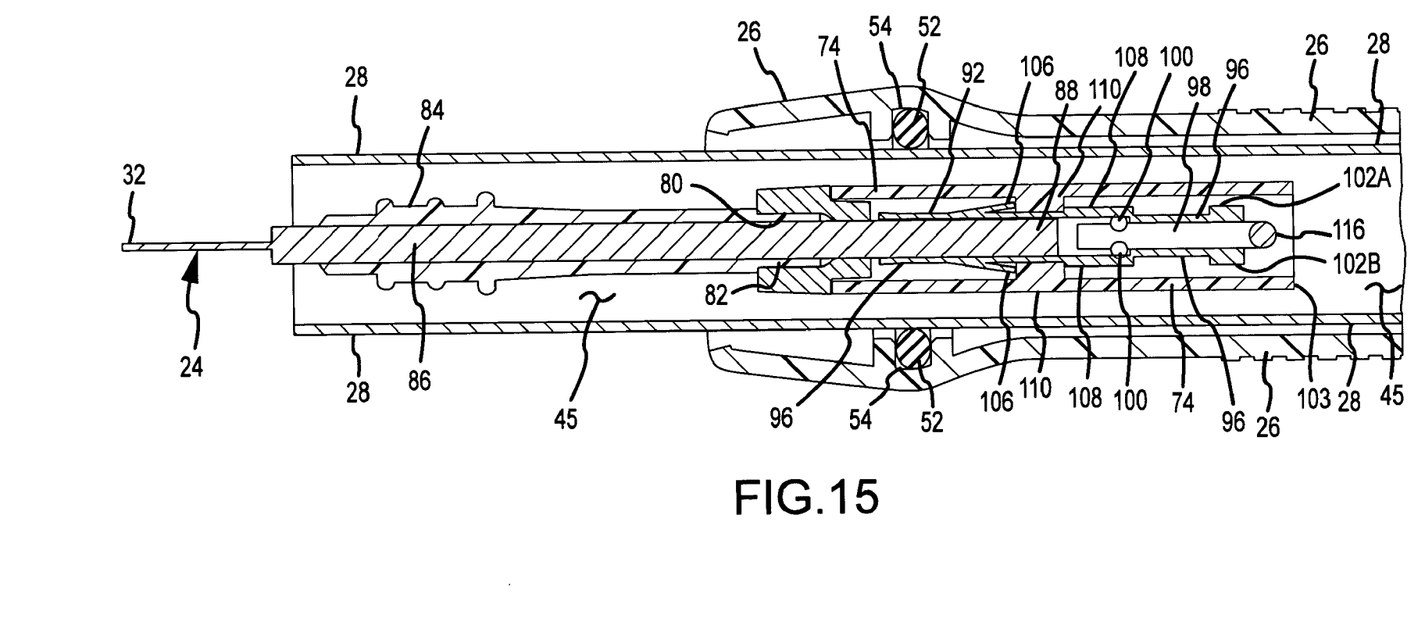
FIG. 15 is a cross-sectional view taken substantially in the plane of line 15-15 in FIG. 6.

The socket member 76 assumes a generally tubular configuration as shown in FIGS. 8, 11, 13 and 15. A distal or forward end 92 of the socket member 76 is generally cylindrically shaped and is adapted to receive and contact the rear end 88 of the electrode body 86 (FIGS. 7 and 15). A proximal or rear end 94 of the socket member 76 also includes a rear cylindrical portion 96 into which a forward or distal end 98 of the anchor rod 78 is inserted (FIGS. 11, 13 and 15). The forward end 98 of the anchor rod 78 is formed with two diametrically opposite extension knobs 100 (FIGS. 11, 14 and 15). The extension knobs 100 are permanently deformed into the outside cylindrical surface of the rod 78. The rear cylindrical portion 96 is crimped around the rod immediately behind the extension knobs 100. Withdrawal of the forward end 98 of the rod 78 from within the rear cylindrical portion 96 is prevented by contact of the extension knobs 100 with the forward edge of the cylindrical portion 96. In addition, two clasps 102A and 102B at the extreme rear end 94 of the socket member 76 are bent around the cylindrical exterior surface of the rod 78 to assist in permanently retaining the forward end 98 of the rod 78 to the socket member 76.

Figure 12:
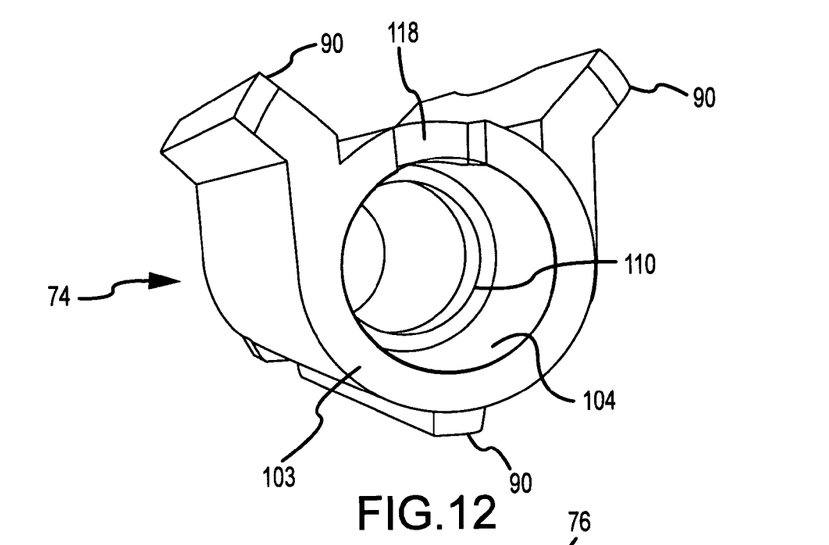
FIG. 12 is a perspective view of a collet member of the electrode anchor unit shown in FIGS. 10 and 11.

The socket member 76 is inserted at a rear end 103 of the collet member 74 through a cylindrical opening 104, shown in FIGS. 12 and 15. A middle portion of the socket member 76 includes tangs 106 which extend outward on opposite sides of the cylindrical portion 96 and fins 108 which also extend outward and are displaced longitudinally toward the rear end 94 of the socket member 76 relative to the tangs 106. The tangs 106 are resiliently deflectable outward from the cylindrical portion 96. When deflected inward by the insertion of the socket member 76 within the collet member 74, the tangs 106 assist in retaining the rod 78. The fins 108 are relatively rigid. An internal ridge 110 (FIG. 12) extends into the cylindrical opening 104 at location midway between the forward and rear ends of the collet member 74.

Upon insertion of the cylindrical portion 96 of the socket member 76 into the cylindrical opening 104 from the rear end of the collet member 74, the tangs 106 deflect inwardly upon encountering the internal ridge 110. Continued insertion of the socket member 76 eventually locates the rear edges of the tangs 106 in front of a front edge of the internal ridge 110, at which point the resiliency of the tangs 106 causes them to move outward against the wall of the opening 104. Simultaneously, the forward edges of the fins 108 contact a rear edge of the internal ridge 110.

With the tangs 106 flexed outward in abutment with the front edge of the internal ridge 110 and the fins 108 abutting the rear edge of the internal ridge 110, as shown in FIG. 15, the socket member 76 is rigidly held within the collet member 74. Rearward movement of the socket member 76 out of the cylindrical opening 104 is inhibited because the rear edges of the tangs 106 contact the front edge of the internal ridge 110. Continued forward movement of the socket member 76 within the cylindrical opening 104 is inhibited because the front edges of the fins 108 contact the rear edge of the internal ridge 110. Thus, longitudinal movement of the socket member 76 relative to the collet member 74 is restricted by the tangs 106 and the fins 108.

Rotational movement of the of the socket member 76 within the cylindrical opening 104 of the collet member 74 is prevented by an offset bend 112 in the anchor rod 78, as shown in FIGS. 10-11. The offset bend 112 separates the forward end 98 from a central portion 114 of the anchor rod 78. The offset bend 112 displaces the central portion 114 of the anchor rod 78 radially or laterally relative to the forward end 98. A radially-extending portion 116 of the anchor rod 78 at the offset bend 112 extends outward immediately at the most rearward edge of the rear end 94 of the socket member 76 through a notch 118 formed in the rear end 103 of the collet member 74. Rotation of the collet member 74 relative to the rod is impossible because the notch 118 contacts the radially extending portion 116 of the anchor rod 78. In addition, rotational movement of the socket member 76 within the collet member 74 is prevented by the secure mechanical connection of the rear end 94 of the socket member 76 to the forward end 98 of the anchor rod 78, as previously described, and by the frictional contact of the tangs 106 and fins 108 with the collet member 74 at the internal ridge 110.

A rear end 120 of the anchor rod 78 includes a right angle bend 122 which causes an end portion 124 of the rod 78 to extend radially relative to the central portion 114 of the rod 78, as shown in FIGS. 7-11. The end portion 124 extends into a rod support socket 126 which is formed in the housing half 26B. Locating the radially extending end portion 124 in the rod support socket 126 creates torsional resistance against rotation of the anchor rod 78, and the offset bend 112 which contacts the notch 118 transfers that torsional resistance to the collet member 74. In this manner, rotational forces applied on the electrode 24 are resisted by the interaction of the radial end portion 124 of the anchor rod 78 with the rod support socket 126 at the rear end 120 of the anchor rod 78 and by the interaction of the radial portion 116 of the offset bend 112 at the forward end 98 of the anchor rod 78.

The electrode anchor unit 72 thus prevents the longitudinal and rotational movement of the collet member 74 and the electrode 24 connected within the collet member 74 relative to the pencil housing 26. However, the electrode anchor unit 72 does not inhibit the longitudinal extension and retraction of the suction tube 28. The central portion 114 of the anchor rod 78 is laterally or radially displaced from the inner surface of the suction tube, and therefore does not contact the suction tube during extension and retraction movement. The radially extending rear end portion 124 of the anchor rod 78 connects to the rod support socket 126 at a position rearward of the most rearward retracted position of the suction tube 28 and therefore does not interfere with the longitudinal rearward movement of the suction tube. Forward or extended movement of the suction tube 28 is restricted by contact of a rear ridge 128 formed on the exterior surface of the suction tube 28 with the O-ring 52 residing in the groove 54 in the housing halves 26A and 26B (FIG. 8).

Because the ribs 90 of the collet member 74 are different lengths and because of the offset bend 112 in the anchor rod and 78, the electrode 24 is attached to the collet member 74 at a radially offset position from the center axis of the cylindrical suction to 28 as shown in FIG. 9. Despite this radial offset, sufficient space exists within the interior passageway 45 of the suction tube 28 to evacuate the smoke, debris and other electrosurgical byproducts created by the tip of the electrode conducting the RF current into the tissue.

The improvements and advantages of the present invention are significant. The electrode anchor unit 72 effectively allows the suction tube 28 to be selectively extended and retracted relative to different length electrodes that may be used with the electrosurgical pencil 20. The slidable suction tube which can be adjusted to the desired position to efficiently remove smoke, debris and other electrosurgical byproducts from the surgical site, or the slidable suction tube can be adjusted to permit access by the electrode into confined surgical sites, or the slidable suction tube can be adjusted to provide enhanced vision of the surgical site during the procedure. The benefits of adjusting the slidable suction tube are obtained with a variety of different length electrodes that can be used with the pencil 20. The electrode anchor unit 72 effectively resists rotational and longitudinal movement of the electrode 24, thereby allowing the electrode 24 to be manipulated effectively by manipulation of the pencil 20.

This is particularly advantageous with respect to bending an electrode to perform a special surgical procedure, since the bent portion of the electrode will not rotate relative to the housing 26 of the pencil 20, thereby allowing the surgeon to control the bent end of the electrode by controlling the pencil itself. In general, the electrode anchor unit 72 is an effective structure for maintaining electrodes stationary within a slidable suction tube.

The significance of the previously discussed and other improvements and advantages will become more apparent upon gaining a full appreciation of the ramifications and improvements of the present invention. A preferred embodiment of the invention and many of its improvements have been described with a degree of particularity. The description is of a preferred example of implementing the invention, and the description is not necessarily intended to limit the scope of the invention. The scope of the invention is defined by the following claims.

The invention claimed is:

1. An electrosurgical pencil for delivering electrical energy from an electrode to tissue at an electrosurgical site and for evacuating electrosurgical byproducts from the site created by delivering the electrical energy to the tissue, comprising:
a pencil housing;
a suction tube movably positioned at the housing and defining an interior passageway which surrounds the electrode and through which the byproducts are evacuated, the suction tube having a distal end which moves in extension and retraction outside of the housing and relative to the electrode, the suction tube also having a proximal end which remains within the housing during the extension and retraction movement of the suction tube;
an electrode anchor unit operatively connected to the housing within the interior passageway of the suction tube to permit the extension and retraction of the suction tube while remaining stationary relative to the housing with respect to the extension and retraction movement of the suction tube, the electrode anchor unit including a socket member by which to connect and disconnect the electrode;
an airflow connector on the housing through which to communicate low-pressure air to the interior passageway of the suction tube for evacuating the byproducts from the surgical site through the interior passageway; and
an electrical connector connected to the socket member by which to deliver the electrical energy to the electrode; and wherein the electrode anchor unit further comprises:
a collet member which supports the socket member, the collet member including contact structures which movably contact the suction tube within the interior passageway; and
an anchor rod extending from the collet member and the socket member through the interior passageway and connecting to the housing at a location beyond the proximal end of the suction tube to avoid interfering with the extension and retraction movement of the suction tube, the anchor rod maintaining the collet member and the socket member stationary relative to the housing with respect to the extension and retraction movement of the suction tube.

2. An electrosurgical pencil as defined in claim 1, wherein:
the anchor rod includes a forward end connected to the collet member and the socket member and a rear end connected to the housing, the connections at the forward and rearward ends of the anchor rod substantially inhibiting rotational movement of the collet member and the socket member relative to the housing within the interior passageway.

3. An electrosurgical pencil as defined in claim 2, wherein:
the socket member further includes a clasp which folds around the forward end of the anchor rod.

4. An electrosurgical pencil as defined in claim 2, wherein:
the anchor rod includes a middle portion between the forward end and the rear end of the anchor rod; and
the forward end of the anchor rod includes an offset bend which creates a radial portion of the anchor rod, and the collet member includes a notch through which the radial portion of the forward end of the anchor rod extends by which to resist relative torsion between the middle portion of the anchor rod and the collet member and the socket member.

5. An electrosurgical pencil as defined in claim 4, wherein:
the radial portion of the forward end of the anchor rod constitutes a first radial portion;
the rear end of the anchor rod includes a bend which defines a second radial portion; and
the housing includes a rod support socket located proximally of the proximal end of the suction tube which receives the second radial portion of the anchor rod by which to resist relative torsion between the middle portion of the anchor rod and the rear end of the anchor rod.

6. An electrosurgical pencil as defined in claim 1, wherein:
the anchor rod is electrically conductive;
the electrical connector which delivers the electrical energy to the electrode includes the electrically conductive anchor rod; and
the socket member is electrically conductive and conducts the electrical energy to the electrode.

7. An electrosurgical pencil as defined in claim 6, wherein:
the collet member defines an interior opening which receives the socket member; and
the socket member includes a tang which contacts the collet member within the interior opening to retain the socket member within the interior opening.

8. An electrosurgical pencil as defined in claim 7, wherein:
the interior opening of the collet member includes an internal ridge which protrudes into the interior opening;
the socket member includes a fin which is longitudinally displaced from the tang; and
the socket member is retained within the interior opening of the collet member by contact of the tang with one edge of the internal ridge and by contact of the fin with an opposite edge of the internal ridge.

9. An electrosurgical pencil as defined in claim 1, wherein:
the contact structures of the collet member comprise a plurality of ribs extending radially outward from the collet member at circumferentially displaced locations around the collet member, spaces between the ribs permitting passage of the byproducts through the interior passageway.

10. An electrosurgical pencil as defined in claim 9, wherein:
one of the ribs extends radially outward from the collet member to a different extent than another one of the ribs; and
the socket member positions the electrode to extend along a longitudinal axis which is offset from a center point of the interior passageway of the suction tube.

11. An electrosurgical pencil as defined in claim 1, wherein:
the socket member accepts and connects to electrodes having different lengths; and the extent of the extension and retraction movement of the suction tube is sufficient to position the distal end of the suction tube adjacent to a tip end of each of the different length electrodes.

12. An electrosurgical pencil for delivering electrical energy from an electrode to tissue at an electrosurgical site and for evacuating electrosurgical byproducts from the site created by delivering the electrical energy to the tissue, comprising:
   a pencil housing;
   a suction tube movably positioned at the housing and defining an interior passageway which surrounds the electrode and through which the byproducts are evacuated, the suction tube having a distal end which moves in extension and retraction movement outside of the housing and relative to the electrode and also having a proximal end which remains within the housing during the extension and retraction movement of the suction tube, the interior passageway defined by an interior surface of the suction tube;
   an electrode anchor unit operatively connected to the housing within the interior passageway of the suction tube to permit the extension and retraction movement of the suction tube while remaining stationary relative to the housing with respect to the extension and retraction movement of the suction tube, the electrode anchor unit including a socket member by which to connect and disconnect the electrode;
   an airflow connector on the housing through which to communicate low-pressure air to the interior passageway of the suction tube for evacuating the byproducts from the surgical site through the interior passageway; and
   an electrical connector connected to the socket member by which to deliver the electrical energy to the electrode; and wherein the electrode anchor unit further comprises:
   a plurality of ribs extending radially outward from the electrode anchor unit at circumferentially displaced locations, spaces between the ribs permitting movement of the byproducts through the interior passageway, the plurality of ribs extending into sliding contact with the interior surface of the suction tube to maintain the electrode anchor unit spaced in a fixed lateral location within the interior passageway separated from the suction tube during the extension and retraction movement of the suction tube.

13. An electrosurgical pencil as defined in claim 12, wherein the electrode anchor unit further comprises:
   an anchor rod extending through the interior passageway and connecting to the housing at a location beyond the proximal end of the suction tube to avoid interfering with the extension and retraction movement of the suction tube, the anchor rod maintaining the electrode anchor unit stationary relative to the housing with respect to the extension and retraction movement of the suction tube.

14. An electrosurgical pencil as defined in claim 13, wherein:
   the anchor rod includes a forward end connected to the collet member and a rear end connected to the housing, the connections at the forward and rearward ends of the anchor rod substantially inhibiting rotational movement of the collet member relative to the housing within the interior passageway.

15. An electrosurgical pencil as defined in claim 12, wherein:
   the socket member accepts and connects to electrodes having different lengths; and
   the extent of the extension and retraction movement of the suction tube is sufficient to position the distal end of the suction tube adjacent to a tip end of each of the different length electrodes.

16. An electrosurgical pencil as defined in claim 12, wherein:
   the plurality of ribs comprises at least three ribs.

* * * * *